(12) United States Patent
Lidgren et al.

(10) Patent No.: US 8,420,127 B2
(45) Date of Patent: Apr. 16, 2013

(54) BONE SUBSTITUTE COMPOSITION

(75) Inventors: Lars Lidgren, Lund (SE); Malin Nilsson, Hudiksvall (SE)

(73) Assignee: Bone Support AB, Lund (SE)

( * ) Notice: Subject to any disclaimer, the term of this patent is extended or adjusted under 35 U.S.C. 154(b) by 769 days.

(21) Appl. No.: 10/547,671

(22) PCT Filed: Mar. 5, 2004

(86) PCT No.: PCT/SE2004/000328
§ 371 (c)(1),
(2), (4) Date: Oct. 16, 2006

(87) PCT Pub. No.: WO2004/078223
PCT Pub. Date: Sep. 16, 2004

(65) Prior Publication Data
US 2007/0041906 A1    Feb. 22, 2007

Related U.S. Application Data

(60) Provisional application No. 60/455,549, filed on Mar. 19, 2003.

(30) Foreign Application Priority Data

Mar. 5, 2003    (SE) ........................................ 0300620

(51) Int. Cl.
A61K 9/14         (2006.01)
A61K 33/00        (2006.01)
A61F 2/00         (2006.01)
A61F 13/00        (2006.01)

(52) U.S. Cl.
USPC ........... 424/602; 424/601; 424/489; 424/422; 424/9.32

(58) Field of Classification Search .......................... None
See application file for complete search history.

(56) References Cited

U.S. PATENT DOCUMENTS

| | | |
|---|---|---|
| 949,163 A | 2/1910 | Stapley |
| 1,644,173 A | 10/1927 | Carr |
| 1,865,912 A | 7/1932 | Horn |
| 2,545,017 A | 3/1951 | Billingsley |
| 3,367,783 A | 2/1968 | Billerbeck |
| 3,475,010 A | 10/1969 | Cook et al. |
| 3,688,765 A | 9/1972 | Gasaway |
| 3,837,379 A | 9/1974 | McDonald et al. |
| 3,965,910 A | 6/1976 | Fischer |
| 4,001,323 A | 1/1977 | Felder et al. |
| 4,139,605 A | 2/1979 | Felder et al. |
| 4,240,425 A | 12/1980 | Akhavi |
| 4,269,331 A | 5/1981 | Watson |
| 4,338,925 A | 7/1982 | Miller |
| 4,348,377 A | 9/1982 | Felder et al. |
| 4,487,766 A | 12/1984 | Mach |
| 4,496,342 A | 1/1985 | Banko |
| 4,583,974 A | 4/1986 | Kokernak |
| 4,619,655 A | 10/1986 | Hanker et al. |
| 4,673,296 A | 6/1987 | Sjogren |
| 4,676,655 A | 6/1987 | Handler |
| 4,721,390 A | 1/1988 | Lidgren |
| 4,752,479 A | 6/1988 | Briggs et al. |
| 4,832,500 A | 5/1989 | Brunold et al. |
| 4,994,442 A | 2/1991 | Gil et al. |
| 5,047,030 A | 9/1991 | Draenert |
| 5,071,040 A | 12/1991 | Laptewicz, Jr. |
| 5,073,362 A | 12/1991 | Blaszkiewicz et al. |
| 5,149,368 A | 9/1992 | Liu et al. |
| 5,168,757 A | 12/1992 | Rabenau et al. |
| 5,232,024 A | 8/1993 | Williams |
| 5,262,166 A | 11/1993 | Liu et al. |
| 5,269,785 A | 12/1993 | Bonutti |
| 5,281,265 A | 1/1994 | Liu |
| 5,328,262 A | 7/1994 | Lidgren et al. |
| 5,342,441 A | 8/1994 | Mandai et al. |
| 5,360,823 A | 11/1994 | Griffel et al. |
| 5,403,318 A | 4/1995 | Boehringer et al. |
| 5,447,711 A | 9/1995 | Almen et al. |
| 5,462,722 A | 10/1995 | Liu et al. |

(Continued)

FOREIGN PATENT DOCUMENTS

| | | |
|---|---|---|
| DE | 44 09 610 A1 | 9/1995 |
| EP | 0 023 992 | 2/1981 |

(Continued)

OTHER PUBLICATIONS

Aebli, N. et al., "Cardiovascular Changes During Multiple Vertebroplasty With and Without Vent-Hole," *SPINE* (2003) 28(14):1504-1512.

Engqvist, H. et al., "Chemical Stability of a Novel Injectable Bioceramic for Stabilisation of Vertebral Compression Fractures," *Trends Biomater. Artif. Organs* (2008) 21(2):98-106.

Ima-Nirwana, S. et al., "Palm vitamin E improves bone metabolism and survival rate in thyrotoxic rats," *Gen. Pharmacol.* (1999) 32:621-626.

Kirby, B. S. et al., "Acute Bronchospasm Due to Exposure to Polymethylmethacrylate Vapors During Percutaneous Vertebroplasty," *AJR* (2003) 180:543-544.

Koessler, M. J. et al., "Fat and Bone Marrow Embolism During Percutaneous Vertebroplasty," *Anesth. Analg.* (2003) 97:293-294.

Komath, M., et al., "On the development of an apatitic calcium phosphate bone cement," *Bull. Mater. Sci.* (2000) 23(2):135-140.

Lidgren, L. "Bone Substitutes," *Karger Gazette* (2003) 65:1-4.

Nilsson, M. et al. "Biodegradation and biocompatability of a calcium sulphate-hydroxyapatite bone substitute," *J. of Bone & Joint Surgery (Br)* (2004) 86-B:120-125.

Bohner, M. et al. "Effects of Sulfate Ions on the in vitro Properties of the β-TCP-MCPM-Water Mixtures. Preliminary in vivo Results," *Ceramic Transactions* (1995) 48, 245-259.

(Continued)

*Primary Examiner* — Elizabeth C Kemmerer
*Assistant Examiner* — Regina M Deberry
(74) *Attorney, Agent, or Firm* — Finnegan, Henderson, Farabow, Garrett & Dunner, L.L.P.

(57) ABSTRACT

An injectable bone mineral substitute material composition with the capability of being hardened in a body fluid in vivo, which comprises at least one calcium phosphate component and at least one calcium sulfate component as a dry mixture mixed with an aqueous liquid, and at least one accelerator, the at least one calcium sulfate component being particulate hardened calcium sulfate, which has a specified particle size that is in order to confer injectability to the composition. The invention also concerns the bone mineral substitute material produced from the composition as well as methods and uses thereof.

36 Claims, 3 Drawing Sheets

U.S. PATENT DOCUMENTS

| | | |
|---|---|---|
| 5,501,520 A | 3/1996 | Lidgren et al. |
| 5,549,380 A | 8/1996 | Lidgren et al. |
| 5,551,778 A | 9/1996 | Hauke et al. |
| 5,605,885 A | 2/1997 | Bernton et al. |
| 5,614,206 A | 3/1997 | Randolph et al. |
| 5,650,108 A | 7/1997 | Nies et al. |
| 5,665,066 A | 9/1997 | Fischer |
| 5,681,873 A | 10/1997 | Norton et al. |
| 5,695,742 A | 12/1997 | Felder et al. |
| 5,698,186 A | 12/1997 | Weeks |
| 5,797,873 A | 8/1998 | Franz et al. |
| 5,829,875 A | 11/1998 | Hagel et al. |
| 5,837,752 A | 11/1998 | Shastri et al. |
| 5,842,786 A | 12/1998 | Solomon |
| 5,866,100 A | 2/1999 | Tournier et al. |
| 5,871,549 A | 2/1999 | Jayashankar et al. |
| 5,891,423 A | 4/1999 | Weeks |
| 5,965,772 A | 10/1999 | Desantis |
| 5,997,544 A | 12/1999 | Nies et al. |
| 6,018,094 A | 1/2000 | Fox |
| 6,018,095 A | 1/2000 | Lerch et al. |
| 6,062,722 A | 5/2000 | Lake |
| 6,071,982 A | 6/2000 | Wise et al. |
| 6,074,358 A | 6/2000 | Andrew et al. |
| 6,075,067 A | 6/2000 | Lidgren |
| 6,080,801 A | 6/2000 | Draenert et al. |
| 6,118,043 A | 9/2000 | Nies et al. |
| 6,120,174 A | 9/2000 | Hoag et al. |
| 6,206,957 B1 | 3/2001 | Driessens et al. |
| 6,231,615 B1 | 5/2001 | Preissman |
| 6,248,110 B1 | 6/2001 | Reiley et al. |
| 6,251,139 B1 | 6/2001 | Lin et al. |
| 6,309,420 B1 | 10/2001 | Preissman |
| 6,365,218 B1 | 4/2002 | Borschel et al. |
| 6,431,743 B1 | 8/2002 | Mizutani et al. |
| 6,440,138 B1 | 8/2002 | Reiley et al. |
| 6,447,809 B1 * | 9/2002 | Krumhar et al. ............... 424/602 |
| 6,485,428 B1 | 11/2002 | Enk |
| 6,488,651 B1 | 12/2002 | Morris et al. |
| 6,586,009 B1 | 7/2003 | Lidgren |
| 6,596,904 B1 | 7/2003 | Dunn et al. |
| 6,689,375 B1 | 2/2004 | Wahlig et al. |
| 6,706,069 B2 | 3/2004 | Berger |
| 6,706,273 B1 | 3/2004 | Roessler |
| 6,716,216 B1 | 4/2004 | Boucher et al. |
| 6,719,761 B1 | 4/2004 | Reiley et al. |
| 6,723,334 B1 | 4/2004 | McGee et al. |
| 6,736,537 B2 | 5/2004 | Coffeen et al. |
| 6,740,090 B1 | 5/2004 | Cragg et al. |
| 6,897,339 B2 | 5/2005 | Turchetta et al. |
| 7,160,306 B2 | 1/2007 | Matsuzaki et al. |
| 7,393,342 B2 | 7/2008 | Henniges et al. |
| 7,417,077 B2 | 8/2008 | Lidgren et al. |
| 7,524,103 B2 | 4/2009 | McGill et al. |
| 7,935,121 B2 | 5/2011 | Lidgren et al. |
| 7,938,572 B2 | 5/2011 | Lidgren et al. |
| 7,972,630 B2 | 7/2011 | Lidgren |
| 2001/0012968 A1 | 8/2001 | Preissman |
| 2001/0051670 A1 | 12/2001 | Goupil et al. |
| 2002/0055143 A1 | 5/2002 | Bell et al. |
| 2002/0076378 A1 | 6/2002 | Wolfe et al. |
| 2002/0156483 A1 | 10/2002 | Voellmicke et al. |
| 2002/0169506 A1 | 11/2002 | Matsushima et al. |
| 2003/0028251 A1 | 2/2003 | Mathews |
| 2003/0050702 A1 | 3/2003 | Berger |
| 2003/0055512 A1 | 3/2003 | Genin et al. |
| 2003/0109883 A1 | 6/2003 | Matsuzaki et al. |
| 2003/0161858 A1 | 8/2003 | Lidgren |
| 2004/0006347 A1 | 1/2004 | Sproul |
| 2004/0048947 A1 | 3/2004 | Lidgren et al. |
| 2004/0049202 A1 | 3/2004 | Berger |
| 2004/0151751 A1 | 8/2004 | Cooper |
| 2004/0191897 A1 | 9/2004 | Muschler |
| 2004/0244651 A1 | 12/2004 | Lemaitre et al. |
| 2005/0015074 A1 | 1/2005 | Trombley, III |
| 2005/0023171 A1 | 2/2005 | Delaney et al. |
| 2005/0105385 A1 | 5/2005 | McGill et al. |
| 2005/0119746 A1 | 6/2005 | Lidgren |
| 2005/0128868 A1 | 6/2005 | Vries |
| 2005/0197629 A1 | 9/2005 | Conway |
| 2005/0241535 A1 | 11/2005 | Bohner |
| 2005/0251149 A1 | 11/2005 | Wenz |
| 2005/0257714 A1 | 11/2005 | Constantz et al. |
| 2005/0287071 A1 | 12/2005 | Wenz |
| 2006/0004358 A1 | 1/2006 | Serhan et al. |
| 2006/0036211 A1 | 2/2006 | Solsberg et al. |
| 2006/0041033 A1 | 2/2006 | Bisig et al. |
| 2006/0122621 A1 | 6/2006 | Truckai et al. |
| 2007/0041906 A1 | 2/2007 | Lidgren et al. |
| 2007/0161943 A1 | 7/2007 | Lidgren et al. |
| 2007/0217282 A1 | 9/2007 | Lidgren et al. |
| 2008/0065088 A1 | 3/2008 | Hughes et al. |
| 2008/0161752 A1 | 7/2008 | Rajala et al. |
| 2008/0318862 A1 * | 12/2008 | Ashman et al. ............... 514/12 |
| 2010/0249753 A1 | 9/2010 | Gaisser et al. |

FOREIGN PATENT DOCUMENTS

| | | |
|---|---|---|
| EP | 0 109 310 B1 | 5/1984 |
| EP | 0 308 364 A2 | 9/1988 |
| EP | 0 495 284 A1 | 7/1992 |
| EP | 0 639 382 A1 | 2/1995 |
| EP | 0 639 382 B1 | 2/1995 |
| EP | 0 657 208 A1 | 6/1995 |
| EP | 0 520 690 B1 | 11/1995 |
| EP | 0 807 432 B1 | 11/1997 |
| EP | 0 950 420 A2 | 10/1999 |
| EP | 1 002 513 | 5/2000 |
| EP | 1 155 704 A1 | 11/2001 |
| EP | 1 208 850 A1 | 5/2002 |
| EP | 1 132 061 B1 | 8/2004 |
| ES | 2 178 556 | 12/2002 |
| GB | 2 239 818 A | 7/1991 |
| JP | 64-22256 A | 1/1989 |
| JP | 64-22257 A | 1/1989 |
| JP | 1-139516 | 6/1989 |
| JP | 5-168692 A | 7/1993 |
| JP | 5-507862 A | 11/1993 |
| JP | 9-502368 | 3/1997 |
| JP | 2935708 B2 | 6/1999 |
| JP | 2000-000295 A | 1/2000 |
| JP | 2000-159564 | 6/2000 |
| JP | 2001-106638 A | 4/2001 |
| JP | 2001-510078 A | 7/2001 |
| JP | 2001-517997 T | 10/2001 |
| JP | 2002-058736 A | 2/2002 |
| JP | 2002-325831 A | 11/2002 |
| JP | 2003-507090 A | 2/2003 |
| SE | 8903538 | 4/1991 |
| WO | WO 85/01727 | 4/1985 |
| WO | WO 88/06023 | 8/1988 |
| WO | WO 87/05521 | 3/1989 |
| WO | WO 89/03695 | 5/1989 |
| WO | WO 91/17722 | 11/1991 |
| WO | WO 95/07108 | 3/1995 |
| WO | WO 96/39202 | 12/1996 |
| WO | WO 91/00252 | 1/1997 |
| WO | WO 97/38676 A1 | 10/1997 |
| WO | WO 97/47334 | 12/1997 |
| WO | WO 99/17710 | 4/1999 |
| WO | WO 99/62570 | 12/1999 |
| WO | WO 99/65597 A1 | 12/1999 |
| WO | WO 00/02597 | 1/2000 |
| WO | WO 00/45867 | 8/2000 |
| WO | WO 01/34216 | 5/2001 |
| WO | WO 02/05861 | 1/2002 |
| WO | WO 02/058755 A2 | 8/2002 |
| WO | WO 02/080033 A1 | 10/2002 |
| WO | WO 03/037165 A2 | 5/2003 |
| WO | WO 03/041753 | 5/2003 |
| WO | WO 03/053488 | 7/2003 |
| WO | WO 2004/000374 | 12/2003 |
| WO | WO 2004/002615 A1 | 1/2004 |
| WO | WO 2004/026377 A1 | 4/2004 |
| WO | WO 2006/041365 A1 | 4/2006 |

OTHER PUBLICATIONS

Bohner, M. "New hydraulic cements based on α-tricalcium phosphate-calcium sulfate dihydrate mixtures," *Biomaterials* (2004) 25, 741-749.

Mirtchi, A. A. et al. "Calcium phosphate cements: action of setting regulators on the properties of the β-tricalcium phosphate-monocalcium phosphate cements," *Biomaterials* (1989) 10(9), 634-638.

Nilsson, M. et al. "Characterization of a novel calcium phosphate/sulphate bone cement," *J. Biomedical Materials Research* (2002) 61(4), 600-607.

Nilsson, M. et al. "New Perspectives of Bioactives Calcium Phosphate Cements for Biomedical Applications," *Research Centre in Biomedical Engineering*, Dept. of Material Science and Metallurgy, Universitat Politècnica de Catalunya, Avda, Diagonal 647, Barcelona, E-08028, Spain, pp. 95-99, Nov. 2000.

Cabañas, M. V. "Setting Behavior and in Vitro Bioactivity of Hydroxyapatite/Calcium Sulfate Cements," *Chem. Mater.* (2002) 14, 3550-3555.

Lidgren, L. "Bone Substitutes," *Karger Gazette* (2002) 65:1-4.

Cahn, R.W., ed. Materials Science and Technology: A Comprehensive Treatment, 1992, vol. 14, VCH, Weinheim, pp. 70-109.

Elliott, J. C. "General Chemistry of the Calcium Orthophosphates," in Structure and Chemistry of the Apatites and Other Calcium Orthophosphates, 1994, Elsevier: Netherlands, Chapter 1, pp. 1-9.

Eromosele et al., "Characterization and viscosity parameters of seed oils from wild plants," Science Direct: Bioresource Technology, 86/2:203-205 (2003).

Nilsson et al., "The Effect of Aging an Injectable Bone Graft Substitute in Simulated Body Fluid," Key Engineering Materials, vols. 240-242 (2003), pp. 403-406.

De Robertis et al., "Solubility of some calcium-carboxylic ligand complexes in aqueous solution," Talanta (1995) 42:1651-1662.

Bohner, M., "Physical and chemical aspects of calcium phosphates used in spinal surgery," Eur. Spine J. (2001) 10;S114-S121.

Damien, C.J. "Investigation of a hydroxyapatite and calcium sulfate composite supplemented with an osteoinductive factor," Student Research Award in the Graduate Degree Candidate Category, 16th Annual Meeting of the Society for Biomaterials, Charleston, SC, May 20-23, 1990; Journal of Biomedical Materials Research, vol. 24, 639-654 (1990).

English abstract of EP 1 002 513 from Espacenet, May 24, 2000.

English abstract of JP 2000-159564 from Espacenet, Jun. 13, 2000.

English language Translation of Japanese Patent Application No. 2002-511792, (p. 1-7) Sep. 22, 2011.

Office Action and English language translation thereof for Japanese Patent Application 2001-574164, corresponding to U.S. Appl. No. 10/257,561 dated Feb. 2, 2011; (10 pages).

Office Action in copending U.S. Appl. No. 12/585,194 dated Aug. 11, 2011, (16 pages).

Parsons, John R., et al., "Osteoconductive Composite Grouts for Orthopedic Use" in Annals New York Academy of Sciences (1988) pp. 190-207.

\* cited by examiner

BONE SUBSTITUTE COMPOSITION

This application is a national stage application under 35 U.S.C. §371 of international application number PCT/SE2004/000328, filed on Mar. 5, 2004, which claims priority to Swedish application number 0300620-2, filed on Mar. 5, 2003, and claims the benefit of U.S. Provisional Application No. 60/455,549, filed Mar. 19, 2003.

TECHNICAL FIELD

The invention refers to a composition for an artificial bone mineral substitute material as well as a bone mineral substitute material produced therefrom. More precisely, the invention relates to an injectable bone mineral substitute material composition with the capability of being hardened in a body fluid in vivo, which comprises at least one calcium phosphate component and at least one calcium sulfate component as a dry mixture mixed with an aqueous liquid, and at least one accelerator, the at least one calcium sulfate component being particulate hardened calcium sulfate, which has a specified particle size in order to confer injectability to the composition.

BACKGROUND ART

The life expectancy of the world population has increased tremendously during the last 50 years. Our population is living longer than ever. The next ten years, it has been forecasted that there will be more people over 60 years of age than less than twenty years of age in Europe. More people will need medical help for diseases related to age, which will increase the pressure of the hospitals.

Bone is the second most common material to be transplanted after blood. The most reliable method to repair bone defects is to use autogenous bone, i.e. bone taken from another site in the body. However, problems may occur at the second surgical site where the graft is taken. To avoid this extra trauma allografts can be used, i.e. bone graft between individuals of the same species. Allografts have a lower osteogenic capacity than autografts and the rate of new bone formation might be lower. They also have a higher resorption rate, a larger immunogenic response and less revascularisation of the recipient. Allografts must also be controlled for viruses since they can transfer, for example, HIV and hepatitis. The use of allografts is now the most common method for bone transplantation and repairing of bone defects.

To solve the problems of supply, unpredictable strength and risk of infection, synthetic bone substitutes have become a realistic alternative. Thus, the demand for and use of synthetic bone substitutes is increasing rapidly.

Calcium sulfate hemihydrate, $CaSO_4 \cdot \frac{1}{2}H_2O$, was one of the first materials investigated as a substitute for bone grafts. Studies have been undertaken since 1892 to demonstrate its acceptance by the tissues and rapid rate of resorption. It has been concluded that calcium sulfate hemihydrate implanted in areas of subcortical bone produces no further untoward reaction in the tissue than normally is present in a fracture. The new bone growing into calcium sulfate hemihydrate is normal bone. No side effects attributable to the implantation of calcium sulfate hemihydrate have been noted in adjacent tissues or in distant organs.

The most important advantage with calcium sulfate is its excellent biocompatibility. The drawbacks are the rapid resorbtion and low strength, which makes it less useful in larger or non-contained defects and when the fracture healing exceeds 4-6 weeks.

The dissolution rate of calcium sulfate has made it suitable as a carrier for drug release. In U.S. Pat. No. 5,614,206 pellets of calcium sulfate hemihydrate are shown, which are useful for controlled delivery of drugs. On implantation of a human or other animal, the pellets provide sustained and controlled delivery to a local site for periods ranging from 25 to 45 days.

Calcium phosphates, on the other hand, are suitable as bone substitutes because of their bioactive properties, i.e. having an effect on or obtaining response from living tissue. Their resorbtion rate is relatively slow, up to several years.

There are two different categories of calcium phosphates: CaP obtained by precipitation from an aqueous solution at room temperature (low-temperature CaP) and CaP obtained by a thermal treatment (high-temperature CaP).

Hydroxyapatite (HA) is the most stable calcium phosphate and the primary non-organic component of bone. Most of the bone graft substitutes on the market are made of hydroxyapatite. High temperature treated hydroxyapatite is highly crystalline and the least soluble of the calcium phosphates.

Hydroxyapatite and tri-calcium phosphate are the most common calcium phosphates used to fill bone defects and as implant coatings. Their resorbtion rate is relatively slow, from six months to several years. It is possible to increase the rate of degradation slightly by increasing the surface area of the material, decreasing the crystallinity and the crystal perfection and decreasing the size of crystals and grains in the material. A higher resorbtion rate can be preferable to encourage bone formation.

However, the biological characteristics and the anatomic site of implantation are also important for the behavior and outcome of the implant. The success of a biomaterial in one specific application does not guarantee its universal acceptance.

Bone mineral substitute materials can be prepared as a paste which can be injected directly into a fracture site. The paste is injected into the void in the bone and, upon hardening, an implant is obtained which conforms to the contours of the gap and supports the cancellous bone. Both calcium sulfate and hydroxyapatite materials have been extensively investigated as a possible alternative to autogenous bone grafts to help restore osseous defects of bone and fixation of bone fracture.

In this connection it is important that a complete stability is obtained as quickly as possible during or after surgery in order to prevent motions at site of healing. This especially applies to fractures, but also when filling of a bone cavity or replacing bone lost during tumor removal the healing is inhibited by movements and the in-growth of new bone is prevented. Thus, the injected material must cure fast and adhere firmly to the bone tissue.

However, during or after surgery complications, such as infections, can arise. Cavities may also be previously infected and have to be treated with for example antibiotics.

It is also of importance that the hardened material is so similar in structure to the bone so that it can be gradually resorbed by osteoclasts and replaced by new bone. This process can be facilitated if the hardened cement is provided with pores, which can transport nutrients and provide vascular ingrowth allowing new bone formation.

M. Bohner et al. disclosed at the Sixth World Biomaterials Congress Transactions (15-20/5 2000) a method to obtain an open macroporous calcium phosphate block by using an emulsion of a hydrophobic lipid (oil) in an aqueous calcium phosphate cement paste or an emulsion of an aqueous calcium phosphate cement paste in oil. After setting, the cement block was sintered at 1250° C. for 4 hours. Likewise, CN 1193614 shows a porous calcium phosphate bone cement for repairing human hard tissue. The cement contains pore-forming agent which may be a non-toxic surfactant, or a nontoxic slightly soluble salt, acidic salt and alkaline salt.

However, a high temperature treatment (>1000° C.) is normally required in order to burn out the added substances. Thus, the emulsion technique cannot yet be used to make bone substitutes that set in vivo. Trials to mix mannitol and sucrose crystals with calcium phosphate have been performed in order to obtain biphasic bone substitute pastes, where one phase dissolves to provide porosity in the set material. Another technique to obtain pores is the addition of air-entraining agents that stabilize the air bubbles created in the paste during mixing, a porous set material thus being provided (Sarda et al., Bioceramics 2002; 218(2):335).

Studies have also been made on mixtures of the above mentioned bone mineral substitute materials. U.S. Pat. No. 4,619,655 discloses a bone mineral substitute material comprising a mixture of calcium sulfate hemihydrate and calcium phosphate ceramic particles, preferably composed of hydroxyapatite, or tricalcium phosphate or mixtures thereof. According to this document, the calcium sulfate hemihydrate was completely resorbed within a few weeks and replaced by connective tissue when material composed of $^{50}/_{50}$ mixtures of hydroxyapatite/calcium sulfate hemihydrate were implanted into experimentally created defects in rat mandible. The hydroxyapatite was not resorbed and some particles were eventually completely surrounded by bone. It was therefore concluded that the calcium sulfate hemihydrate acted as filler and scaffold for the incorporation of hydroxyapatite into bone.

A study presented on the "Combined Orthopaedic Research Societies Meeting", Sept. 28-30, 1998, Hamamatsu, Japan, also shows additional tests relating to mixtures of calcium sulfate hemihydrate and hydroxyapatite. According to this study a combination of hydroxyapatite particles and calcium sulfate hemihydrate had a viscosity which allowed an easy placement of the implant material and prevented migration of hydroxyapatite particles into surrounding tissues during and after implantation. The experiments showed that calcium sulfate hemihydrate was absorbed in relatively short time, was easily manipulated with hydroxyapatite particles, and did not interfere with the process of bone healing.

WO 9100252 shows a composition which is capable of hardening in blood within about 10-45 min. The composition comprises essentially calcium sulfate hemihydrate with small amounts of calcium sulfate dihydrate. Organic and inorganic materials, such as hydroxyapatite, can also be included in the composition. After hardening, particles of hydroxyapatite are obtained within a calcium sulfate cement. The calcium sulfate cement is dissolved rapidly by aqueous body fluids within four weeks, leaving solid particles of hydroxyapatite.

Likewise, such particles of hydroxyapatite within a calcium sulfate cement are obtained by means of the method shown in WO 9117722. The composition for use as an animal implant comprises calcium sulfate hemihydrate, calcium phosphate, and sodium sulfate. The calcium phosphate is hydroxyapatite and the sodium sulfate enables the composition to be used in the presence of blood or other body fluids.

In WO 200205861 an injectable composition is shown, which is useful for a bone mineral substitute material. The dry powder of the composition comprises calcium sulfate hemihydrate, calcium phosphate and at least one accelerator. In contact with an aqueous liquid the composition will harden during surgery with accompanying early control of fracture fragment movement. A stable lasting implant is provided, which has a higher mechanical strength than trabecular bone, and the implant obtains with time a porous as well as irregular structure for bone in growth.

THE INVENTION

The object of the invention is to provide a composition for a bone mineral substitute material, which is injectable, which hardens in a body fluid in vivo during surgery, and which provides a stable lasting implant over a year with high mechanical strength, whereby a porous structure is obtained, which size and formation can be controlled.

Another object of the present invention is to provide such an improved bone mineral substitute composition for filling defects in osteoporotic bone and for additional fracture fixation in substantially cancellous bone, which does not exhibit the drawbacks of high viscosity at delivery.

A further object of the invention is to provide a bone mineral substitute composition, which can be used with minimally invasive surgical techniques, which can be hardened in situ, and which results in stability of any defect geometry.

Still another object of the invention is to provide a bone mineral substitute composition that has excellent biocompatibility as well as favorable biological and rheological properties.

Yet still a further object of the invention is to provide a bone mineral substitute composition that is biodegradable and can be sterilized by radiation or gas without suffering a significant deterioration in properties.

In order to achieve these objects the injectable composition according to the invention has been given the characterizing features of claim 1.

DETAILED DESCRIPTION OF THE INVENTION

Figure 1:
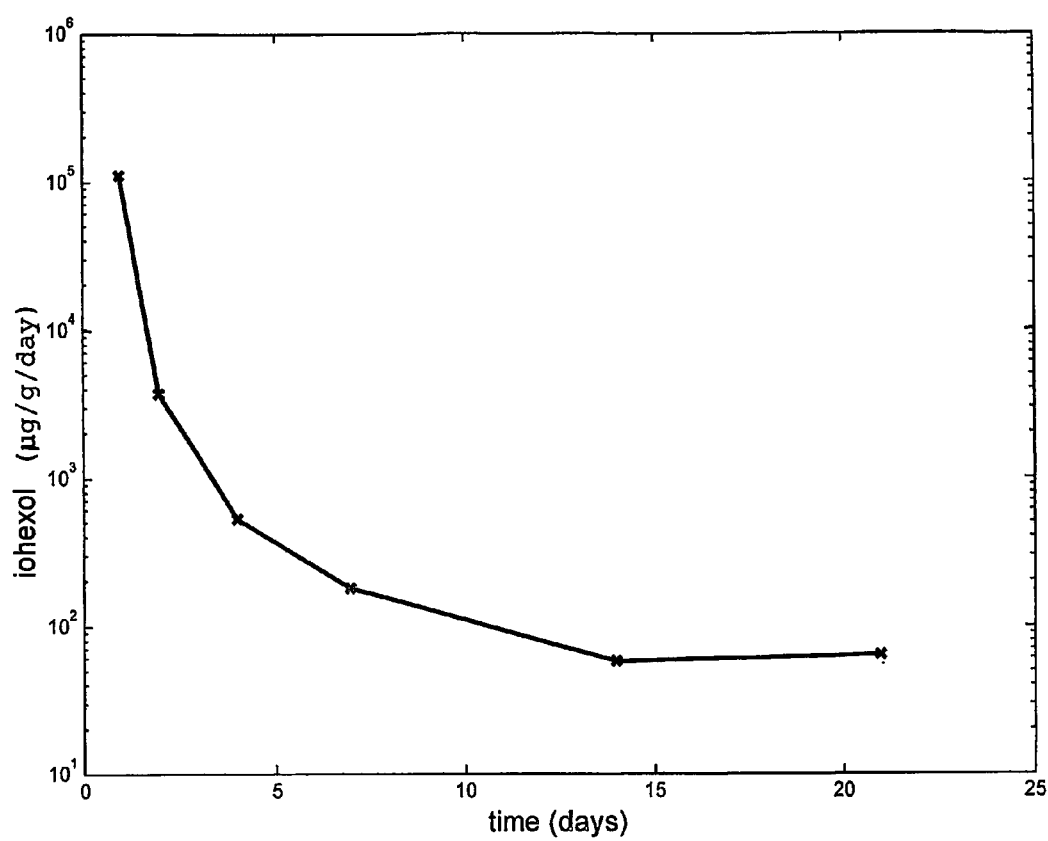
FIG. 1 shows the in vitro release of iohexol from the composition of Example 1 in an isotonic buffer.

According to the invention an injectable composition for a bone mineral substitute material is provided, which has the capability of being hardened in a body fluid in vivo. The injectable composition comprises at least one calcium phosphate component and at least one calcium sulfate component as a dry mixture, and an aqueous liquid mixed with the dry mixture. The at least one calcium sulfate component is particulate hardened calcium sulfate that has a diameter which is less than 100 µm, the injectability of the composition being guaranteed. The composition also comprises at least one accelerator.

The particle diameter of the particulate hardened calcium sulfate is adapted to a size that is sufficiently small to allow for the composition to be injectable. A suitable particle diameter of the particulate hardened calcium sulfate is between 1 and 50 µm, preferably between 1 and 10 µm. This means that the composition can be injected through a needle having a diameter of about 1-2 mm or even less.

The particulate hardened calcium sulfate should comprise up to 60 wt %, preferably 10-40 wt % of the dry mixture of the injectable composition.

Preferably, the particulate hardened calcium sulfate is calcium sulfate dihydrate (gypsum).

The injectability of the composition according to the invention can be further improved in several ways. A pH reducing component can be added to the inventive composition to increase its injectability. Such a pH reducing component is for example ascorbic acid or citric acid. These acids are included in a sterile liquid or a sterile powder of the composition in amounts of 0.1-5 wt %, preferably 0.5-2 wt %.

Another way to further improve the injectability of the composition is to add a biologically compatible oil. The concentration of the oil should in this case be between 0.01 and 5 wt %, preferably between 0.1 and 2 wt %. The oil can either be intermixed with the sterile powder or included in the sterile aqueous liquid of the composition. A suitable oil to be used in the inventive composition is vitamin E. Preferably, the vitamin E is α-tocopherol.

A main aspect of the invention is that the particulate hardened calcium sulfate can comprise at least one additive that is slowly released from the bone mineral substitute material after it has set. The additive can both be non-water soluble and water soluble. An example of a non-water soluble additive is vitamin E.

However, it is preferred that the additive is water soluble. The water soluble additive can have several functions. It can for example be an antioxidant, a vitamin, a hormone, an antibiotic, a cytostatic, a bisphosphonate, a growth factor, or a protein. Advantageously, the at least one water soluble additive is a substance that induces, stimulates and/or accelerates bone formation, such as osteoinductive compounds and/or compounds reducing bone turn over.

Suitable bone inducing substances, which stimulate and/or accelerate bone formation, are growth factors and hormones. Growth factors and derivatives thereof are preferred, which are locally acting.

It is preferred to use growth factors, which are autologous and effective in connection with bone, tendon or cartilage. Such growth factors are for example transforming growth factor (TGF β3), bone morphogenic protein (BMP-2), PTHrP, osteoprotegrin (OPG), Indian Hedgehog, RANKL, basic fibroblast, insulin-like growth factor (IgF1), platelet derived growth factors, and vascular growth factors. These endogenously produced growth factors are used as an additive either as single entities or combined in a growth factor mixture in order to accelerate bone growth. Thus, it is preferred that an endogenously produced bioactive molecule is used as a substance that induces bone formation.

Examples of other bone stimulating compounds are parathyorid hormones and derivatives thereof, estrogenes, progesterones, androgenes, testosterones, calcitonin, somatomedin, and oxytocin, preferably also autologous, but they can also be produced according to procedures known within the art.

The enamel matrix proteins amelin-1, amelin-2 and ameloblastin can also be included as an additive in the particulate calcium sulfate, which are either autologous or extracted from or produced by tissues or cells from other species, or synthetically produced or produced by other living cells or organisms.

Likewise, the cholesterol-lowering compound statin can also be included in order to induce, stimulate and/or accelerate bone formation.

Examples of suitable bone breakdown inhibitors are biphosphonates, osteocalcin, osteonectin and derivatives thereof, which can be included as an additive in the particulate calcium sulfate of the inventive composition and of the resulting substitute.

In addition, other substances that influence the metabolism of bone may also be included in the particulate hardened calcium sulfate component to be slowly released from the resulting artificial bone mineral substitute material. Such substances include calciferols, calcitriols, as well as other D vitamins and derivatives thereof. These compounds help to regulate calcium metabolism and the normal calcification of bones in the body as well as influence the utilization of mineral phosphorus. Natural or synthetically produced prostaglandins, precursors or metabolites to prostaglandins, prostaglandin analogues or compounds that induce or inhibit endogenous prostaglandin production or induce or inhibit prostaglandin metabolism, or compounds that affect the production of precursors or further metabolism of active prostaglandin metabolites, may also be included. Analgesics, such as lidocaine-HCl, bupivacaine-HCl, and ketorolac tromethamine, can also be used as an additive to be liberated from the bone mineral substitute material.

Such additives should preferably be released from the bone mineral substitute material within 6-8 weeks after injection. This can be accomplished by controlling the dissolution of the particulate calcium sulfate in the bone mineral substitute material, the dissolution rate being dependent on the size and the form of the calcium sulfate particles.

The water soluble additive can also be an anti-infectious substance, i.e. a compound with a static or cidal effect against invading foreign living material. Such compounds include natural antibiotics as well as other semisynthetic and synthetic antibacterial or bacteriostatic compounds, which are acting against pathogenic and/or infectious microorganisms, e.g. staphylococci. Examples of antibiotics for bone infections are tetracycline-HCl, vancomycin, tobramycin, gentamycin, and cephalosporin. Cytostatic agents, such as cisplatinum, ifosfamide, methotrexate, doxorubicin-HCl, arsenic trioxide, and retinoids or derivatives thereof can also be used as an additive. The additive can in a similar way be an antiviral compound, an antifungal compound, a tuberculostatic or tuberculocidal compound or an antiparasite compound.

The water soluble additive, which may be included in the particulate calcium sulfate, can also be a non-ionic X-ray contrast agent.

Suitable such agents are conventional water soluble non-ionic X-ray contrast agents, i.e. iodinated aromatic compounds, which have one or several aromatic nuclei that are at least triiodo-substituted. Such agents are shown in U.S. Pat. No. 5,695,742 and comprise CAS (Chemical Abstract Service) registration numbers 31112-62-6 (metrizamide), 60166-93-0 (iopamidol), 78649-41-9 (iomeprol), 73334-07-3 (iopromide), 877771-40-2 (ioversol), 66108-95-0 (iohexol), 89797-00-2 (iopentol), 107793-72-6 (ioxilan), 99139-49-8 (II-1), 75751-89-2 (iogulamide), 63941-73-1 (ioglucol), 63941-74-2 (ioglucamide), 56562-79-9 (ioglunide), 76984-84-0 (MP-7011), 64965-50-0 (MP-7012), 77111-65-0 (MP-10007), 79944-49-3 (VA-7-88), 79944-51-7 (also shown in EP 033426), 79211-10-2 (iosimide), 79211-34-0 (iocibidol), 103876-29-5 (also shown in EP 0177414), 141660-63-1 (iofratol), 92339-11-2 (iodixanol), 79770-24-4 (iotrol), 71767-13-0 (iotasul), 81045-33-2 (iodecol), 143200-04-8 (also shown in WO 92/086), 143199-77-3 (also shown in WO 92/08691), 143200-00-4 (also shown in WO 92/08691), 78341-84-1 (also shown in US 4348377), 122731-47-9 (also shown in EP 0308364), 122731-49-1 (also shown in EP 0308364), 99139-65-8 (also shown in WO 85/01727), 99139-62-5 (also shown in WO 85/01727), and 78341-84-1 (also shown in EP 0023992).

Other such X-ray contrast agents are shown in U.S. Pat. No. 5,447,711 and comprise iotrolan, ioxaglate, iodecimol, and iosarcol. Other suitable contrast agents are iotusal, ioxilane, and iofrotal.

Preferably, the X-ray contrast agent is non-ionic and has a low osmomolality, such as iohexol, iodixanol, ioversol, iopamidol, and iotrolane.

For example, iohexol ($C_{19}H_{26}I_3N_3O_9$) can with advantage be used as an X-ray contrast agent. This substance does not influence bone formation and it has a good biocompatibility in bone. It is used for different purposes in medicine. For example it can be used for patients with kidney failure to determine the rate of plasma clearance by the kidney.

The inventive composition with a non-ionic X-ray contrast agent as a water soluble additive included in the particulate calcium sulfate can in itself be used as an X-ray contrast medium. An additive X-ray effect is obtained by means of the composition according to the invention, since the X-ray contrast ability of its ceramic component is utilized. The inclusion of at least one water soluble non-ionlc X-ray contrast agent in the composition increases the original X-ray density of the X-ray dense bone substitute. Thus, no further ceramic radio contrast agents, such as barium sulfate and zirconium dioxide, have to be included in the injectable composition according to the invention. Such hard ceramic particles will wear joints when torn off from the bone substitute. In the joints they will cause physical damage and eventually result in inflammatory reactions.

Thus, the inventive composition, when it comprises a water soluble non-ionic X-ray contrast agent, can be injected adjacent to joints, and the resulting artificial bone mineral substitute material can be used for bone defects communicating with joints. Such applications include the repair of osteochondral joints defects as well as fractures or bone defects involving a joint.

In addition, the dual origin of X-ray density can be further exploited, for example in order to localize the injected composition and to follow the healing process after implantation of the inventive composition in a human or animal body. When the obtained artificial bone mineral substitute material, which comprises a water soluble non-ionic X-ray contrast agent, is replaced by ingrowing bone, the water soluble agent will slowly disappear. This results in a progressive decline in X-ray density, which can be monitored.

The particulate hardened calcium sulfate is according to the invention mixed with the powdered calcium phosphate component, which is subsequently hardened to a calcium phosphate cement in the bone mineral substitute material.

The term "calcium phosphate cement" refers to the recognized definition (S. E. Gruninger, C. Siew, L. C Chow, A. O'Young, N. K. Tsao, W. E. Brown, *J.Dent. Res.* 63 (1984) 200) of a reaction product of a powder or a mixture of powders which—after mixing with water or an aqueous solution to a paste—at a temperature around room temperature or body temperature react with the formation of a precipitate, which contains crystals of one or more calcium phosphates and which sets by the entanglement of the crystals within the precipitate. Thus, different calcium phosphate products (calcium phosphate cements) can be obtained during the setting reaction in dependence on the component(s) of the powdered calcium phosphate used for the paste in the inventive injectable composition for a bone mineral substitute material.

In the injectable composition according to the invention the at least one calcium phosphate component is a powdered calcium phosphate with the capability of being hardened (cemented) to a calcium phosphate cement when reacting with the aqueous liquid under the influence of the at least one accelerator. The aqueous liquid should comprise between 0.1 and 2 ml, preferably between 0.2 and 0.7 ml per gram of the dry mixture. The aqueous liquid may be provided in an amount that is sufficient for this hardening reaction only.

The aqueous liquid can be distilled water and/or a solution comprising one or several inorganic and/or organic salts.

Under these conditions, the main requirement on an injectable composition for a bone mineral substitute material is fulfilled, i.e. it should have a viscosity so that it can be injected into a bone for 1-5 minutes after the beginning of the mixing procedure. Furthermore, the initial setting time is within 5-25 minutes, which also is a prerequisite for an injectable composition.

Preferably, the at least one calcium phosphate component of injectable composition for a bone mineral substitute material is hardened to a hydroxyapatite (HA). Those reactions, which form hydroxyapatite, i.e. precipitated hydroxyapatite (PHA) or calcium deficient hydroxyapatite (CDHA), can be classified into three groups. The first group consists of calcium phosphates, which are transformed into hydroxyapatite by a hydrolysis process in an aqueous solution (eq. 1-5).

$$5Ca(H_2PO_4) \cdot H_2O \rightarrow Ca_5(PO_4)_3OH + 7H_3PO_4 + 4H_2O \quad (1)$$

$$5CaHPO_4 \cdot 2H_2O \rightarrow Ca_5(PO_4)_3OH + 2H_3PO_4 + 9H_2O \quad (2)$$

$$5Ca_8H_2(PO_4)_6 \cdot 5H_2O \rightarrow 8Ca_5(PO_4)_3OH + 6H_3PO_4 + 17H_2O \quad (3)$$

$$5Ca_3(PO_4)_2 + 3H_2O \rightarrow 3Ca_5(PO_4)_3OH + H_3PO_4 \quad (4)$$

$$3Ca_4(PO_4)_2O + 3H_2O \rightarrow 2Ca_5(PO_4)_3OH + Ca(OH)_2 \quad (5)$$

Precipitated hydroxyapatite is the least soluble calcium phosphate at pH over 4,2. This means that any other calcium phosphate present in an aqueous solution at this pH range will tend to dissolve, with the precipitation of PHA as a product. This hydrolysis process ($Ca(OH)_2$—$H_3PO_4$—$H_2O$) is very slow due to a decrease in supersaturation as the reaction proceeds.

The only calcium phosphate which can react via a hydrolysis process to an apatite without the formation of sub-products is α-tricalcium phosphate (eq. 6), and the apatite formed in this reaction is a calcium deficient hydroxyapatite.

$$3\alpha\text{-}Ca_3(PO_4)_2 + H_2O \rightarrow Ca_9(HPO_4)(PO_4)_5OH \quad (6)$$

The second group of reactions to a hydroxyapatite, i.e. precipitated hydroxyapatite (PHA) or calcium deficient hydroxyapatite (CDHA), is the combinations between TTCP and other calcium phosphates. TTCP is the only calcium phosphate with Ca/P-ratio above 1.67. Thus, this substance can be mixed with other calcium phosphates with lower Ca/P-ratio to obtain PHA or CDHA without the formation of acids or bases as by-products. Theoretically, any calcium phosphate more acid than PHA can react directly with TTCP to form HA or CDHA according to the following chemical reactions.

$$7Ca_4(PO_4)_2O + 2Ca(H_2PO_4)_2 \cdot H_2O \rightarrow 6Ca_5(PO_4)_3OH + 3H_2O \quad (7)$$

$$2Ca_4(PO_4)_2O + Ca(H_2PO_4)_2 \cdot H_2O \rightarrow Ca_9(HPO_4)(PO_4)_5OH + 2H_2O \quad (8)$$

$$Ca_4(PO_4)_2O + CaHPO_4 \cdot 2H_2O \rightarrow Ca_5(PO_4)_3OH + 2H_2O \quad (9)$$

$$3Ca_4(PO_4)_2O + 6CaHPO_4 \cdot 2H_2O \rightarrow 2Ca_9(HPO_4)(PO_4)_5OH + 13H_2O \quad (10)$$

$$Ca_4(PO_4)_2O + CaHPO_4 \rightarrow Ca_5(PO_4)_3OH \quad (11)$$

$$3Ca_4(PO_4)_2O + 6CaHPO_4 \rightarrow 2Ca_9(HPO_4)(PO_4)_5OH + H_2O \quad (12)$$

$$3Ca_4(PO_4)_2O + Ca_8H_2(PO_4)_6 \cdot 5H_2O \rightarrow 4Ca_5(PO_4)_3OH + 4H_2O \quad (13)$$

$$3Ca_4(PO_4)_2O + 3Ca_8H_2(PO_4)_6 \cdot 5H_2O \rightarrow 4Ca_9(HPO_4)(PO_4)_5OH + 14H_2O \quad (14)$$

$$Ca_4(PO_4)_2O + 2Ca_3(PO_4)_2 + H_2O \rightarrow Ca_5(PO_4)_3OH \quad (15)$$

In equations (7) and (8) DCPD is formed as an intermediate reaction product, but with PHA or CDHA at the end of the reaction. Reactions (13), (14), and (15) are all very slow. However, by using the formulas (9)-(12) it is possible to produce a cement which sets and hardens with time at room or body temperature and at a neutral pH.

It is also possible to form PHA as the final hardened product by using mixtures of calcium phosphates with a Ca/P ratio of less than 1.67. This is accomplished by using additional calcium sources, such as $Ca(OH)_2$ or $CaCO_3$, instead of TTCP. One example is the reaction $\beta$-TCP+DCPD+$CaCO_3 \rightarrow$PHA. Initially formed crystals of PHA from a reaction between DCPD and $CaCO_3$ function as binders between $\beta$-TCP particles. When DCPD is consumed the reaction continues between the remaining calcium carbonate and $\beta$-TCP with the formation of PHA. However, it seems that the latter process has a detrimental effect on the mechanical strength of the cement.

It is preferred that the powdered at least one calcium phosphate component with the capability of being hardened to a calcium phosphate cement when reacting with an aqueous liquid is tetracalcium phosphate (TTCP), monocalcium phosphate monohydrate (MCPM), dicalcium phosphate dihydrate (DCPD), anhydrous dicalcium phosphate (DCPA), dicalcium phosphate (DCP), tricalcium phosphate (TCP), or octocalcium phosphate (OCP). Preferably, the calcium phosphate is $\alpha$-tricalcium phosphate.

The powdered at least one calcium phosphate component should comprises 40-98 wt %, preferably 60-90 wt of the dry mixture comprising the calcium phosphate component and the calcium sulfate component.

The powdered calcium phosphate component has to be rapidly hardened with the restricted amount of available water in order to provide a bone substitute with acceptable properties within 15 min after injection. The hardening reaction of this component to a calcium phosphate cement can by means of the composition according to the invention be controlled to set within 18 h as a bone mineral substitute material with a strength of about 30 MPa.

This can be accomplished in different ways. In a preferred embodiment of the invention the water soluble additive is an accelerator for hardening the powdered calcium phosphate to a calcium phosphate cement when reacting with the aqueous liquid. Such an accelerator can be a phosphate salt, for example disodium hydrogen phosphate ($Na_2HPO_4$). The rate of the hardening reaction in vivo can be varied by varying the amount of phosphate salt between 0.01 and 10 wt % of the total composition, the salt being included in the particulate hardened calcium sulfate to be subsequently slowly released therefrom.

The phosphate salt can also be dissolved in the aqueous liquid. In this case, the accelerator should be present in the aqueous liquid at concentrations of 0.1-10 wt %, preferably 1-5 wt %.

The reaction of the powdered calcium phosphate component to a calcium phosphate cement can also be accelerated by adding hardened particulate calcium phosphate cement to the inventive composition as an accelerator. The hardened calcium phosphate cement can be hydroxyapatite (HA), precipitated hydroxyapatite (PHA), or preferably calcium deficient hydroxyapatite (CDHA), or a mixture thereof. It should have a Ca/P ratio between 1.5 and 2. The particulate calcium phosphate cement as an accelerator should have a particle size which is less than 20 µm, preferably less than 10 µm and comprise between 0.1 and 10 wt %, preferably between 0.5 and 5 wt % of the calcium phosphate which is to react with an aqueous liquid.

The different ways of accelerating the reaction of calcium phosphate to calcium phosphate cement can be used either separately or in combination.

Accordingly, the hardening reaction can be adapted to last about 18 h in order to set to a high strength material. During this period of time the already hardened sulfate will confer an initial strength to the implant, and when the setting reaction of calcium phosphate component to a high strength material is completed, a final strength will be obtained. The artificial bone mineral substitute material will retain its stability for 3-4 years.

Each particle of calcium sulfate dihydrate will contain larger amounts of sulfate crystals. When the artificial bone mineral substitute material is resorbed in the body, the water in the blood will ultimately dissolve the crystals of the hardened sulfate ceramic and release any additive therein. It should be noted, that this reaction with several orders of magnitude is very much slower than the hardening reaction of the calcium phosphate component to a calcium phosphate cement.

Additives, which are bound to the sulfate crystals, will be released in vivo together with the calcium sulfate when the body fluid with time comes in contact with the bone mineral substitute material. Thus, the pore formation is accompanied by a controllable slow release of at least one additive in the hardened bone substitute, which has advantageous properties in vivo. Water soluble additives will be released and dissolved to effectively exert their effects at the site of action.

Accordingly, pores, holes and cavities will gradually be formed as the sulfate degrades, which act like lacuna, and the finally set and hardened implant of a high strength material will look like a normal bone. Elongated particles are preferred. This results in that a contact can be obtained between the blood and a majority of the hardened calcium sulfate particles in the bone mineral substitute material, which are dissolved within 6-12 months.

Particles as aggregates of single crystals can also be used in order to provide small distances between each crystal. Such particles of can be provided by particulate calcium sulfate hemihydrate. In this case the $\alpha$-form of calcium sulfate hemihydrate is preferred instead of the $\beta$-form, not only because of its increased mechanical strength but also because of its crystal size.

The water soluble as well as the non-water soluble additive can be included in the particulate hardened calcium sulfate during its preparation. Thus, the water soluble additive at a suitable concentration in a aqueous solution is mixed with calcium sulfate hemihydrate, and the reaction with gypsum as product is allowed to take place:

$$2(CaSO_4 \cdot \tfrac{1}{2}H_2O) + 3H_2O \rightarrow 2(CaSO_4 \cdot 2H_2O) + \text{heat} \quad (16)$$

The structure of gypsum consists of layers of alternate $SO_4^{2-}$ ions strongly bonded to $Ca^{2+}$ and sheets of water molecules, and the additives will bind to the sulfate crystals of the particulate calcium sulfate.

When calcium sulfate hemihydrate is used, the water soluble additive is similarly included in the particulate calcium sulfate during its preparation. The gypsum is in this case ground and heated until about 75% of the water has evaporated, and $CaSO_4 \cdot \frac{1}{2}H_2O$ is obtained. However, the two known forms (α and β) of calcium sulfate hemihydrate are produced differently according to:

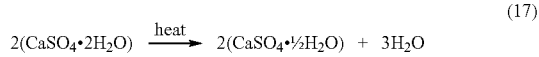

(17)

The α-form is obtained by dehydrating gypsum hydrothermally in the presence of electrolytes. The α-form is produced by dehydrating gypsum in a water atmosphere at temperatures above 100° C. Accordingly, the water soluble additive at a suitable concentration in a aqueous solution is allowed to be present when these reactions take place.

Likewise, the water soluble additive will in a similar way adhere by means of electrostatic interactions with the residual crystal water of the particulate hardened calcium sulfate.

A preferred way to produce the calcium sulfate hemihydrate is to utilize the already prepared particulate dihydrate having a water soluble additive included therein. In this case the ground gypsum is subjected to the necessary heat treatment in for example an autoclave, crystals being produced which can be used as particulate calcium sulfate.

It is obvious that the water soluble additives have to be thermostable if included in the particulate calcium sulfate that is to be transformed into calcium sulfate hemihydrate.

An efficient mixing system must be available in order to prepare the injectable composition according to the invention. The mixing can take place in a conventional cement mixing system and the composition is injected by means of a convenient delivery system. The mixing container is preferably of that type which can suck the aqueous component into the powder component (German Patent 4409610). This Prepack™ system is a closed mixing system for delivery in combination with prepacked components in a flexible foil bag. Other mixing devices can of course also be used, for example two interconnected soft bags that can be adapted to a delivering cylinder.

The formation of air bubbles in the composition, which can interfere with the hardening reaction of the calcium phosphate component and result in a decreased initial mechanical strength of the implanted material during surgery, can be prevented by mixing the inventive composition under conditions of subatmospheric pressure, e.g. in vacuo. However, an atmospheric pressure can also be used. Preferably, the dry mixture of the composition is sterilized by means of radiation before it is mixed with the sterile aqueous liquid.

The hardened bone mineral substitute material can be prefabricated in a suitable shape, e.g. as pellets or balls containing at least one, which allows for the attachment of implants and/or treatment of diseases, etc. In this connection it is preferred that the water soluble additive is a bioactive agent.

Hardened calcium sulfate, on the other hand, is for example produced as massive blocks, which are processed, e.g. grinded, to particles having the specific size that is also suitable for bone ingrowth. The shape of these blocks is of no consequence for the invention.

The invention also concerns a bone mineral substitute material produced from the composition according to the invention. Such an implant can be introduced into an animal or human body after it has been hardened.

The inventive composition, or the bone mineral substitute material itself, can be used in a wide variety of applications, such as fracture healing, prosthetic implants, and implants of foreign materials in other situations. Such situations may comprise filling a gap or a bone void or a pre-existing bone cavity, such as fractures, osteotomy, for the attachment of prostheses or other foreign material, for prosthetic revision surgery, for plastic surgery, for reconstruction surgery, or for cosmetic surgery.

In both cases, the composition as well as the bone mineral substitute material are suitable for local use in tooth pockets and/or bifurcatures to treat periodontitis or to be combined with other treatment options for periodontitis included therein, such as supportive matrix proteins or locally acting growth inducing factors.

Likewise, they can be used together with collagen or other supports, which are of importance for the growth of supportive tissues.

The injectable composition is also mouldable and can thus be used for the filling of maxillar, frontal, ethmoidal, or spheroidal sinuses to allow attachment of screws, needles etc., such as the attachment of tooth implants with a pin or a screw or a needle up through the maxillar sinus.

Furthermore, the injectable composition can be used to fill skeletal defects caused by the removal of orthopedic screws, pins or needles, which are utilized for internal or external fixation of fractures. It is in such occasions preferred that antibiotics are included in the composition as additives.

The injectable composition can also be used together with expanders to create room for a material to be inserted, such as an inflatable balloon or a metal expander that is removed before the introduction of the composition or an expander filled with the composition, or a stent filled with the composition or attached to the bone mineral substitute material.

Accordingly, the invention also concerns a method of implanting a bone substitute to a supportive tissue in a human or non-human animal subject, wherein an injectable composition for a bone mineral substitute material is introduced into said tissue, said injectable composition having the capability of being hardened in a body fluid in vivo and comprises an aqueous liquid;

at least one calcium sulfate component of particulate calcium sulfate; and at least one calcium phosphate component of powdered calcium phosphate with the capability of being hardened to a calcium phosphate cement when reacting with said aqueous liquid under the influence of at least one accelerator, said aqueous liquid being provided in an amount that is sufficient for said hardening reaction only;

said at least one calcium phosphate component and said at least one calcium sulfate component being provided as a dry mixture.

Instrumental or non-instrumental non-invasive or invasive fusion surgery can be performed when utilizing the inventive composition or the bone mineral substitute material itself, for example in connection with the spine or joints, such as finger joints, vertebral joints, shoulder joints, etc.

Another embodiment of the invention, which can be used in connection with the above-mentioned applications, comprises local injection of the composition with a concomitant systemic treatment with a bioactive agent. Such a systemic treatment can be given as single or sustained treatments. Suitable bioactive agents are the above-mentioned water soluble additives that induce, stimulate and/or accelerate bone formation, or inhibit bone degradation, e.g. bone inducing agents, such as parathyroid hormones, growth factors or statins. Likewise, a systemic treatment can be applied with agents that inhibit bone metabolism, such as biphosphonates.

Accordingly, the invention also concerns a method of prophylactic or therapeutic treatment of a disorder related to supportive tissues in a human or non-human animal subject, which method comprises providing to said subject a composition for a bone mineral substitute material with the capability of being hardened in a body fluid in vivo, which comprises
an aqueous liquid;
at least one calcium sulfate component of particulate calcium sulfate; and
at least one calcium phosphate component of powdered calcium phosphate with the capability of being hardened to a calcium phosphate cement when reacting with said aqueous liquid under the influence of at least one accelerator,
said aqueous liquid being provided in an amount that is sufficient for said hardening reaction only;
said at least one calcium phosphate component and said at least one calcium sulfate component being provided as a dry mixture;
while systemically and concomitantly administering a prophylactic or therapeutic amount of at least one bioactive agent.

However, a preferred embodiment of the invention comprises a corresponding local treatment or prophylaxis of a disorder, the injectable composition comprising bioactive agents. This embodiment involves a method of prophylactic or therapeutic treatment of a disorder related to supportive tissues in a human or non-human animal subject, which method comprises providing to said subject a composition for a bone mineral substitute material with the capability of being hardened in a body fluid in vivo, which comprises
an aqueous liquid;
at least one calcium sulfate component of particulate calcium sulfate; and
at least one calcium phosphate component of powdered calcium phosphate with the capability of being hardened to a calcium phosphate cement when reacting with said aqueous liquid under the influence of at least one accelerator,
said aqueous liquid being provided in an amount that is sufficient for said hardening reaction only;
said at least one calcium phosphate component and said at least one calcium sulfate component being provided as a dry mixture;
while concomitantly administering a prophylactic or therapeutic amount of at least one water soluble bioactive agent as an inclusion in said particulate calcium sulfate, which is to be slowly released therefrom.

The method is especially useful for local treatment of infections or infestations in the musculoskeletal system, such as osteomyelitis caused by e.g. bacteria. A combined supportive or osteoconductive treatment and a prophylaxis of skeletal infection can thus be obtained, e.g. in sternotomies, prosthetic implants, reconstructive surgery, trauma surgery, cancer surgery, cosmetic surgery, and oro-maxillar surgery.

This method is also useful for local treatment with cytostatic agents, such as in musculoskeletal tumors, e.g. metastases in vertebrae from breast or prostatic cancers demanding treatment with a supportive material that concomitantly gives a possibility for local treatment with tumor-inhibiting agents. Furthermore, it can be used locally together with agents that enhances the clinical effects of irradiation in diseases, such as tumor diseases.

This method can also be used for local and supportive treatment with agents that inhibit bone resorption or stimulate bone formation.

EXAMPLES

The invention will now be further described and illustrated by reference to the following examples, which have been carefully selected in order to encompass the invention. Accordingly, they should not be construed as limiting the invention in any way.

Example 1

Slow Release of an X-ray Contrast Agent

A composition according to the invention was prepared, which contained 40 wt % hydroxyapatite and 60 wt % particulate hardened calcium sulfate, which had been previously doped with 5 wt % of the non-ionic X-ray contrast agent iohexol (12.1 g iohexol/100 g particles).

The release of iohexol from the calcium sulfate based material in an isotonic buffer was followed in vitro. The results are shown in FIG. 1.

The release from day 1 is the total release during that day. In total, more than 94% of the doped agent was released.

Example 2

Slow Release of an Antibiotic

Compositions according to the invention was prepared, which contained 80 wt % hydroxyapatite and 20 wt % particulate hardened calcium sulfate, which had been previously doped with two different concentrations (3 and 6 wt %) of the antibiotic gentamicin sulfate.

Figure 2:
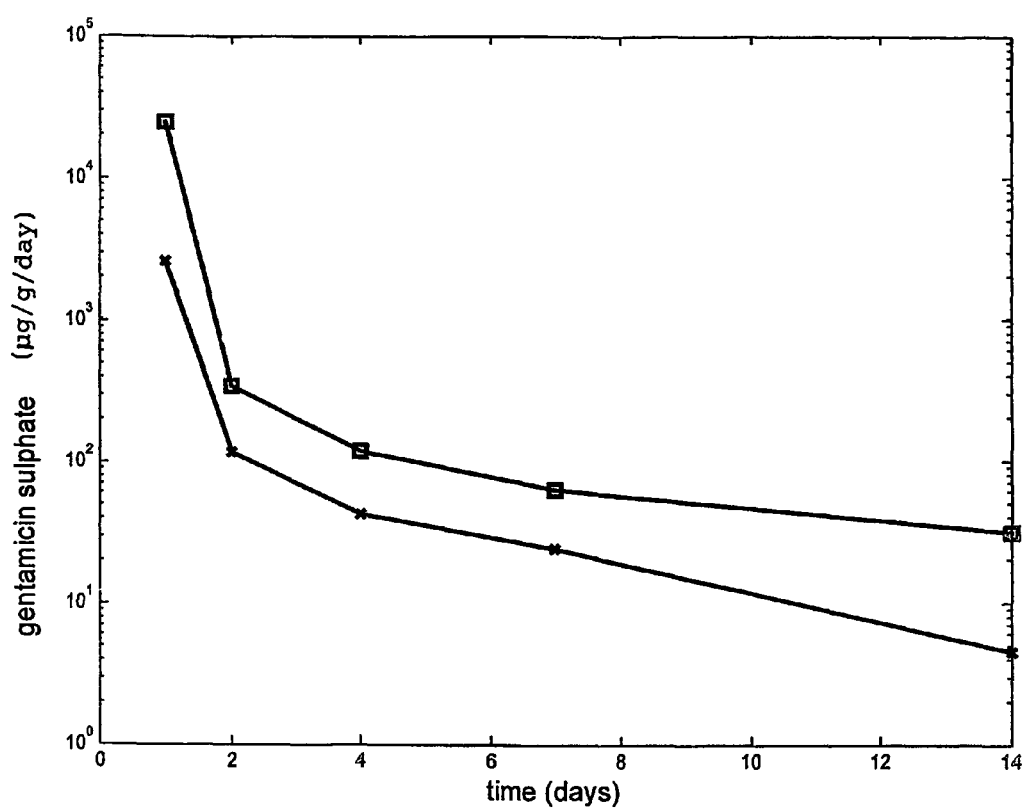
FIG. 2 shows the in vitro release of gentamicin from two compositions of Example 2 in an isotonic buffer.

The release of gentamicin from the calcium sulfate based material in an isotonic buffer was followed in vitro. The results are shown in FIG. 2.

The release was faster with 6 wt % (□) than with 3 wt % (*) gentamicin.

A comparison was made between the release of gentamicin from particles of hardened calcium sulfate only, which had been previously doped with two different gentamicin concentrations as above.

Figure 3:
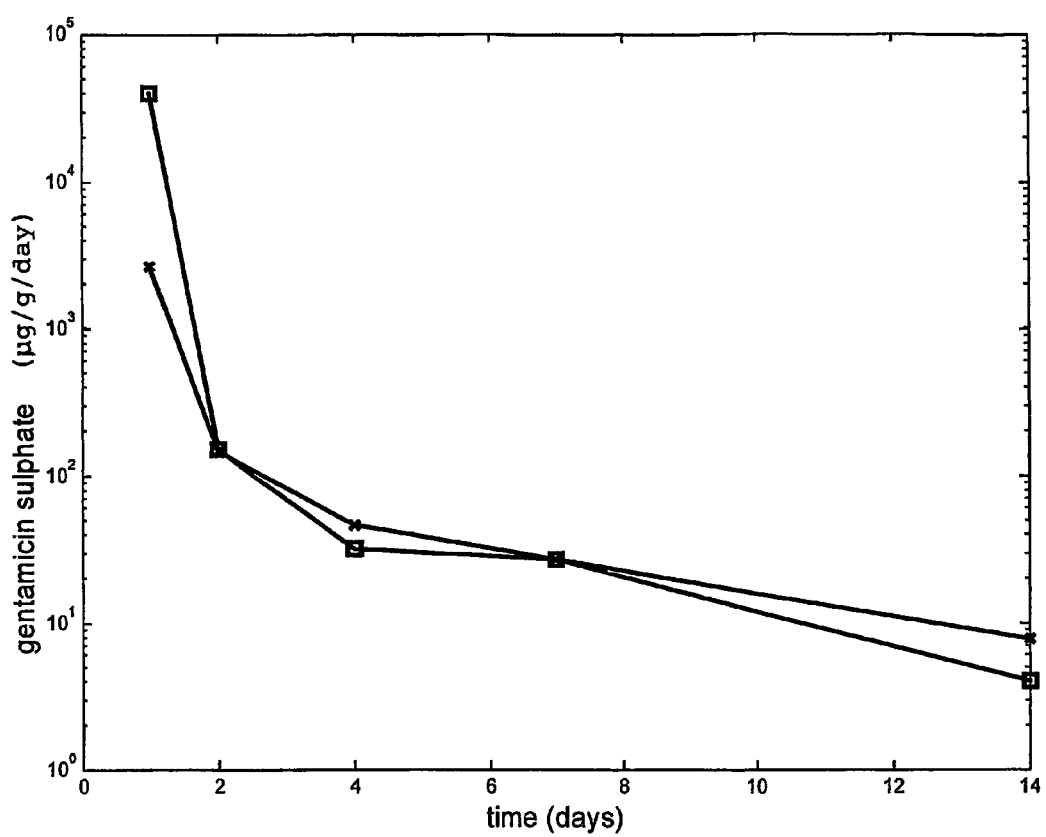
FIG. 3 shows the in vitro release of gentamicin from the comparative compositions of Example 2 in an isotonic buffer.

The release of gentamicin from the calcium sulfate particles in an isotonic buffer was followed in vitro. The results are shown in FIG. 3.

Example 3

Injection in vivo

A composition according to the invention was prepared, which had a particle size distribution of less than 100 μm.

The composition was successfully injected into narrow piglet trabecular bone channels as well as into spine of human cadaver and set in situ.

Microphotographs reveal that the composition has entered and penetrated the microchannels of bone, which have a size of 200-300 μm or less.

The invention claimed is:
1. A composition comprising:
a) at least one calcium phosphate component in the form of a powder capable of being hardened into a cement when contacted with an aqueous liquid;
b) at least one hardened particulate calcium sulfate dihydrate component containing
a prophylactic or therapeutic amount of at least one water soluble bioactive agent, wherein said at least one hardened particulate calcium sulfate dihydrate component is present in an amount ranging from 10 wt % to 60 wt % of said composition and has a particle diameter of less than 100 μm; and c) at least one accelerator chosen from disodium hydrogen phosphate (Na$_2$HPO$_4$), calcium phosphate cement, precipitated hydroxyapatite (PHA), and calcium deficient hydroxyapatite (CDHA), or a mixture thereof, and wherein the at least one hardened particulate calcium sulfate dihydrate component is prepared according to a process comprising reacting calcium sulfate hemihydrate, the at least one water soluble bioactive agent, and water.

2. The composition of claim 1, wherein said at least one hardened particulate calcium sulfate dihydrate component is present in an amount ranging from 10 wt % to 40 wt % of said composition.

3. The composition of claim 1, wherein said at least one hardened particulate calcium sulfate dihydrate component has a particle diameter between 1 μm and 50 μm.

4. The composition of claim 1, wherein said at least one hardened particulate calcium sulfate dihydrate component has a particle diameter between 1 μm and 10 μm.

5. The composition of claim 1, wherein said at least one calcium phosphate component is present in an amount ranging from 40 wt % to 90 wt % of said composition.

6. The composition of claim 1, wherein said at least one calcium phosphate component is present in an amount ranging from 60 wt % to 90 wt % of said composition.

7. The composition of claim 1, wherein said at least one calcium phosphate component is chosen from tetracalcium phosphate (TTCP), monocalcium phosphate monohydrate (MCPM), dicalcium phosphate dihydrate (DCPD), anhydrous dicalcium phosphate (DCPA), dicalcium phosphate (OCP), tricalcium phosphate (TCP), and octocalcium phosphate (OCP).

8. The composition of claim 7, wherein said at least one calcium phosphate component is tricalcium phosphate (TCP).

9. The composition of claim 1, wherein said at least one water soluble bioactive agent is chosen from an endogenously produced bioactive molecule; an antioxidant; a vitamin chosen from calciferons, calcitrols, other D vitamins and derivatives thereof; a cytostatic agent; a protein; an analgesic, an antiviral, an antifungal or tuberculostatic/tuberculocidal compound; an antiparasite compound; a natural antibiotic; a semisynthetic or synthetic antibacterial; a bacteriostatic compound; an antiinfectious substance; a natural or synthetically produced prostaglandin; a precursor or metabolite to prostaglandin; a prostaglandin analogue or compound that induces or inhibits endogenous prostaglandin production or induces or inhibits prostaglandin metabolism; a compound that affects the production of precursors or further metabolism of active prostaglandin metabolites; a growth factor which is optionally endogenously produced; an enamel matrix protein; biophosphonates; osteocalcin; osteonectin or derivatives thereof; an osteoinductive compound; a hormone which is optionally autologous; a growth factor or a derivative thereof; and a statin.

10. The composition of claim 1, wherein said at least one water soluble bioactive agent is an antibiotic.

11. The composition of claim 10, wherein said antibiotic is gentamycin.

12. The composition of claim 1, wherein said at least one accelerator is hydroxyapatite (HA).

13. The composition of claim 1, wherein said calcium phosphate cement accelerator is present in an amount between 0.1 wt % and 10 wt % of said at least one calcium phosphate component.

14. The composition of claim 1, wherein said calcium phosphate cement accelerator has a Ca/P ratio between 1.5 and 2.

15. The composition of claim 1, wherein said calcium phosphate cement accelerator has a particle diameter of less than 20 μm.

16. The composition of claim 1, wherein said composition further comprises a pH reducing component.

17. A method of substituting bone comprising
(a) injecting a composition comprising a composition according to claim 1 and an aqueous liquid into a gap in the bone, a bone void, and/or a pre-existing bone cavity; and
(b) allowing said composition to harden.

18. A method of substituting bone comprising
placing a cement composition prepared from the hardening reaction of a composition according to claim 1 and
an aqueous liquid, into a gap in the bone, a bone void, and/or a pre-existing bone cavity.

19. A method of preparing an injectable composition comprising contacting
at least one calcium phosphate component;
at least one hardened particulate calcium sulfate dihydrate component containing a prophylactic or therapeutic amount of at least one water soluble bioactive agent, wherein said at least one hardened particulate calcium sulfate dihydrate component is present in an amount ranging from 10 wt % to 60 wt % of the total weight of the components other than the aqueous liquid before said combination and has a particle diameter of less than 100 μm; and
at least one accelerator chosen from disodium hydrogen phosphate (Na$_2$HPO$_4$), calcium phosphate cement, precipitated hydroxyapatite (PHA), and calcium deficient hydroxyapatite (CDHA), or a mixture thereof,
with an aqueous liquid, wherein the resulting composition is in the form of an injectable composition, and
wherein the at least one hardened particulate calcium sulfate dihydrate component is prepared according to a process comprising reacting calcium sulfate hemihydrate, the at least one water soluble bioactive agent, and water.

20. The method of claim 19, wherein the aqueous liquid comprises an accelerator.

21. The method of claim 20, wherein said aqueous liquid comprises a water soluble non-ionic X-ray contrast agent.

22. The method of claim 21, wherein said water soluble non-ionic X-ray contrast agent is iohexol.

23. A system comprising:
(a) a first unit comprising at least one calcium phosphate component, at least one hardened particulate calcium sulfate dihydrate component containing at least one water soluble bioactive agent, and at least one accelerator chosen from disodium hydrogen phosphate (Na$_2$HPO$_4$), calcium phosphate cement, precipitated hydroxyapatite (PHA), and calcium deficient hydroxyapatite (CDHA), or a mixture thereof,
wherein said at least one hardened particulate calcium sulfate dihydrate component is present in an amount ranging from 10 wt % to 60 wt % of said composition of said first unit and has a particle diameter of less than 100 μm; and
wherein the at least one hardened particulate calcium sulfate dihydrate component is prepared according to a process comprising reacting calcium sulfate hemihydrate, the at least one water soluble bioactive agent, and water; and (b) a second unit comprising an aqueous liquid, wherein the composition of said first unit and the liquid of said second unit are not in contact.

24. The system of claim 23, wherein the aqueous liquid comprises an accelerator.

25. The system of claim 23, wherein said at least one hardened particulate calcium sulfate dihydrate component is present in an amount ranging from 10 wt % to 40 wt % of said composition of said first unit.

26. The system of claim 23, wherein said at least one hardened particulate calcium sulfate dihydrate component has a particle diameter between 1 μm and 50 μm.

27. The system of claim 23, wherein said at least one hardened particulate calcium sulfate dihydrate component has a particle diameter between 1 μm and 10 μm.

28. The system of claim 23, wherein said at least one calcium phosphate component is present in an amount ranging from 40 wt % to 90 wt % of said composition of said first unit.

29. The system of claim 23, wherein said at least one calcium phosphate component is present in an amount ranging from 60 wt % to 90 wt % of said composition of said first unit.

30. The system of claim 23, wherein said at least one calcium phosphate component is chosen from tetracalcium phosphate (TTCP), monocalcium phosphate monohydrate (MCPM), dicalcium phosphate dihydrate (DCPD), anhydrous dicalcium phosphate (DCPA), dicalcium phosphate (OCP), tricalcium phosphate (TCP), and octocalcium phosphate (OCP).

31. The system of claim 30, wherein said at least one calcium phosphate component is tricalcium phosphate (TCP).

32. The system of claim 23, wherein said at least one water soluble bioactive agent is chosen from an endogenously produced bioactive molecule; an antioxidant; a vitamin chosen from calciferons, calcitriols, other D vitamins and derivatives thereof; a cytostatic agent; a protein; an analgesic, an antiviral, an antifungal or tuberculostatic/tuberculocidal compound; an antiparasite compound; a natural antibiotic; a semi-synthetic or synthetic antibacterial; a bacteriostatic compound; an antiinfectious substance; a natural or synthetically produced prostaglandin; a precursor or metabolite to prostaglandin; a prostaglandin analogue or compound that induces or inhibits endogenous prostaglandin production or induces or inhibits prostaglandin metabolism; a compound that affects the production of precursors or further metabolism of active prostaglandin metabolites; a growth factor which is optionally endogenously produced; an enamel matrix protein; biophosphonates; osteocalcin; osteonectin or derivatives thereof; an osteoinductive compound; a hormone which is optionally autologous; a growth factor or a derivative thereof; and a statin.

33. The system of claim 23, wherein said at least one water soluble bioactive agent is an antibiotic.

34. The system of claim 33, wherein said antibiotic is gentamycin.

35. The system of claim 23, wherein said system further comprises an accelerator.

36. The system of claim 35, wherein said accelerator is chosen from disodium hydrogen phosphate ($Na_2HPO_4$), calcium phosphate cement, precipitated hydroxyapatite (PHA), calcium deficient hydroxyapatite (CDHA), or a mixture thereof.

* * * * *

UNITED STATES PATENT AND TRADEMARK OFFICE
CERTIFICATE OF CORRECTION

| | | |
|---|---|---|
| PATENT NO. | : 8,420,127 B2 | Page 1 of 1 |
| APPLICATION NO. | : 10/547671 | |
| DATED | : April 16, 2013 | |
| INVENTOR(S) | : Lars Lidgren et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1245 days.

Signed and Sealed this
Thirteenth Day of January, 2015

Michelle K. Lee
*Deputy Director of the United States Patent and Trademark Office*